United States Patent
Piplani et al.

(10) Patent No.: US 6,214,038 B1
(45) Date of Patent: *Apr. 10, 2001

(54) METHOD FOR DEPLOYING AN ENDOVASCULAR GRAFT HAVING A BIFURCATION

(75) Inventors: Alec A. Piplani, Mountain View; Dinah B. Quiachon, San Jose; Wesley D. Sterman, San Francisco, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/396,567

(22) Filed: Sep. 15, 1999

Related U.S. Application Data

(63) Continuation of application No. 08/742,311, filed on Nov. 1, 1996, now Pat. No. 6,132,459, which is a continuation of application No. 08/166,069, filed on Dec. 10, 1993, now Pat. No. 5,609,625, which is a continuation of application No. 08/066,414, filed on May 21, 1993, now Pat. No. 5,489,295, which is a continuation of application No. 07/684,018, filed on Apr. 11, 1991, now abandoned.

(51) Int. Cl.[7] .......................................... A61F 2/00
(52) U.S. Cl. ............................................. 623/1.11
(58) Field of Search ................................. 623/1.11, 1.12, 623/1.13, 1.23

(56) References Cited

U.S. PATENT DOCUMENTS

| 2,978,787 | 4/1961 | Liebig . |
| 2,990,605 | 7/1961 | Demsyk . |

(List continued on next page.)

FOREIGN PATENT DOCUMENTS

| 0461791 A1 | 12/1991 | (EP) . |
| 0466518 A3 | 1/1992 | (EP) . |
| 0479557 A1 | 8/1992 | (EP) . |
| 660689 | 5/1979 | (RU) . |
| 8806026 | 8/1988 | (WO) . |
| WO 90/15582 | 12/1990 | (WO) . |

OTHER PUBLICATIONS

Lawrence, Jr. MD et al., Radiologu (1987); pp. 163:357–360, "Percutaneous Endovascular Graft: Experimental Evaluation".

Yoshioka et al., AJR (Oct. 1988); pp. 151:673–676, "Self–Expanding Endovascular Graft: An Experimental Study In Dogs".

Mirich, MD et al., Radiology (1989) pp. 170:1033–1037, "Percutaneously Placed Endovascular Grafts For Aortic Aneurysms: Feasibility Study".

Charnsangavej, MD et al., Radiology (1986); pp. 161:295–298, "Stenosis of the Vena Cava: Preliminary Assessment of Treatment With Expandable Metallic Stents".

Rösch, MD et al., Cancer (1987); pp. 60:1243–1246, "Gianturco Expandable Wire Stents in the Treatment of Superior Vena Cava Syndrome Recurring After Maximum–Tolerance Radiation".

(List continued on next page.)

Primary Examiner—Michael J. Milano
(74) Attorney, Agent, or Firm—Fulwilder Patton Lee & Utecht, LLP

(57) ABSTRACT

Graft having a bifurcation for repairing an aneurysm in the vicinity of an aortic bifurcation in a patient comprising a main tubular body and first and second tubular legs joined to said main body in a bifurcation. The main body and the legs are formed of a flexible surgically implantable material. The main body and each of the first and second legs having an opening therein in communication with the other openings. Expandable spring attachments are secured to the main body adjacent the opening in the main body. An additional expandable spring attachment is secured to one of said legs adjacent the opening in said one leg.

7 Claims, 6 Drawing Sheets

U.S. PATENT DOCUMENTS

| | | |
|---|---|---|
| 3,029,819 | 4/1962 | Starks . |
| 3,096,560 | 7/1963 | Liebig . |
| 3,142,067 | 7/1964 | Liebig . |
| 3,657,744 | 4/1972 | Ersek . |
| 3,908,662 | 9/1975 | Razgulov et al. . |
| 3,945,052 | 3/1976 | Liebig . |
| 4,041,931 | 8/1977 | Elliot et al. . |
| 4,047,252 | 9/1977 | Liebig et al. . |
| 4,140,126 | 2/1979 | Choudhury . |
| 4,193,137 | 3/1980 | Heck . |
| 4,202,349 | 5/1980 | Jones . |
| 4,214,587 | 7/1980 | Sakura, Jr. . |
| 4,517,687 | 5/1985 | Liebig et al. . |
| 4,562,596 | 1/1986 | Kornberg . |
| 4,617,932 | 10/1986 | Kornberg . |
| 4,652,263 | 3/1987 | Herweck et al. . |
| 4,693,249 | 9/1987 | Schenck et al. . |
| 4,728,328 | 3/1988 | Hughes et al. . |
| 4,787,899 | 11/1988 | Lazarus . |
| 4,872,874 | 10/1989 | Taheri . |
| 4,878,906 | 11/1989 | Lindeman et al. . |
| 4,892,539 | 1/1990 | Koch . |
| 4,969,890 | 11/1990 | Sugita et al. . |
| 5,104,399 | 4/1992 | Lazarus . |
| 5,108,424 | 4/1992 | Hoffman, Jr. et al. . |
| 5,127,919 | 7/1992 | Ibrahim et al. . |
| 5,234,447 | 8/1993 | Kaster et al. . |

OTHER PUBLICATIONS

Charnsangavej, MD et al., Radiology (1985); pp. 157:323–324, "Endovascular Stent for Use in Aortic Dissection: An in Vitro Experiment".

Rösch, MD et al., CIRSE, Porto Cervo, Sardinia (1987); pp. 31:100–103, "Modified Gianturco Expandable Wire Stents in Experimental and Clinical Use".

Rösch. MD et al., Radiology (1987); pp. 162:481–485, "Experimental Intrahepatic Portacaval Anastomosis: Use of Expandable Gianturco Stents".

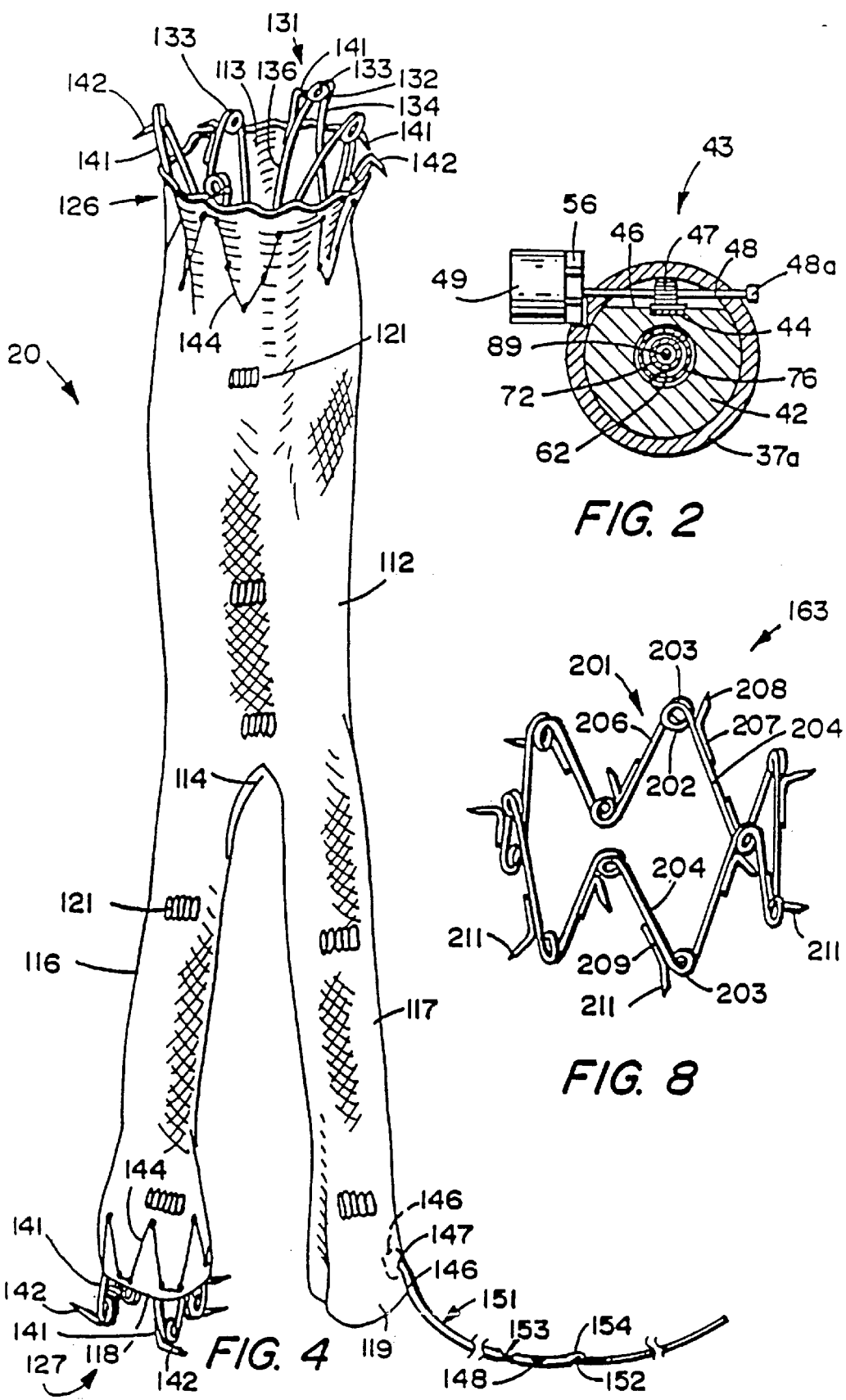

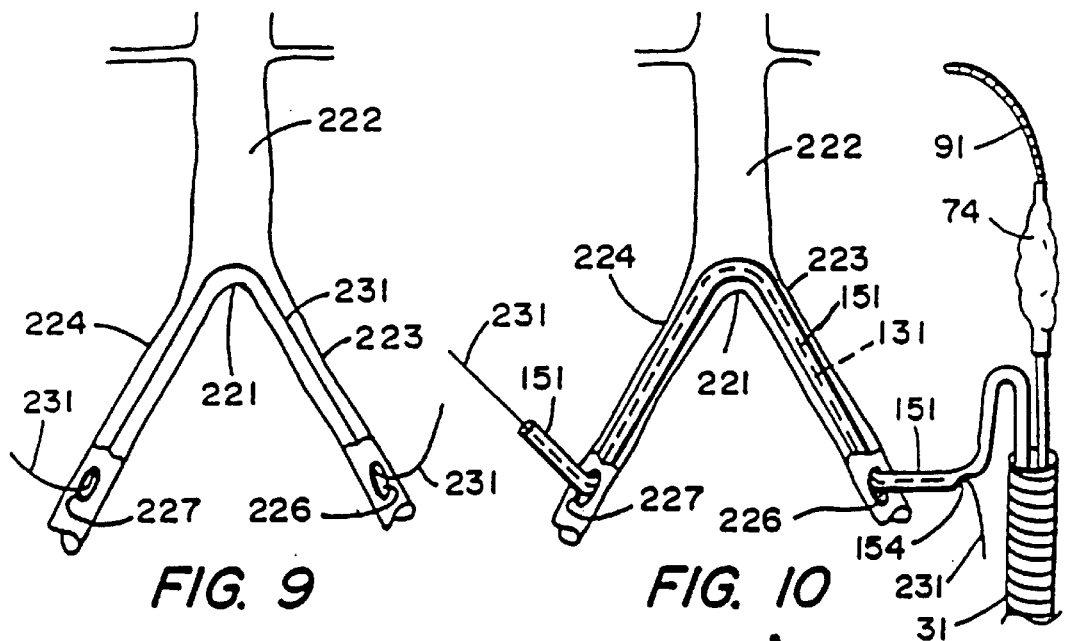
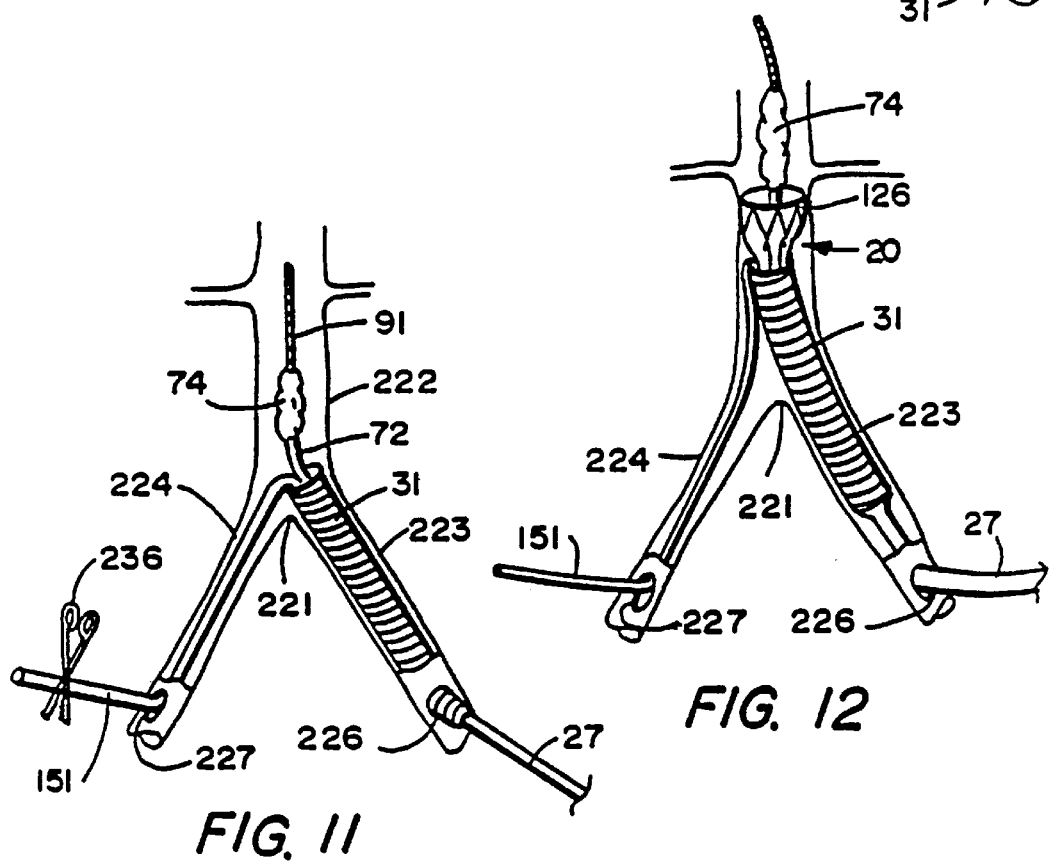
FIG. 9  FIG. 10  FIG. 11  FIG. 12

METHOD FOR DEPLOYING AN ENDOVASCULAR GRAFT HAVING A BIFURCATION

This application is a continuation of application Ser. No. 08/742,311, filed Nov. 1, 1996, now U.S. Pat. No. 6,132,459, which is a continuation of application Ser. No. 08/166,069, filed Dec. 10, 1993, now U.S. Pat. No. 5,609,625, which is a continuation of application Ser. No. 08/066,414, filed May 21, 1993, now U.S. Pat. No. 5,489,295, which is a continuation of application Ser. No. 07/684,018, filed Apr. 11, 1991 now abandoned.

BACKGROUND OF THE INVENTION

This invention relates to an endovascular graft having bifurcation and an apparatus and a method for deploying the same.

In Kornberg U.S. Pat. No. 4,617,932 there is disclosed a bifurcated graft which has two legs with one leg being longer than the other leg. There is also disclosed a device and a method for inserting the graft into an artery. However, there is a need for an improved endovascular bifurcated graft and an apparatus and a method for deploying the same.

SUMMARY OF INVENTION

In general, it is an object of the present invention to provide an endovascular graft having bifurcation and an apparatus and a method for deploying the same which makes it possible to secure the graft firmly in place traversing the aortic bifurcation with an apparatus and method which facilitates rapid deployment and placement of the same.

Another object of the invention is to provide a graft of the above character which has a body portion that can be firmly fixed in place in this aorta and has legs which can be firmly fixed in place in the iliac arteries.

Another object of the invention is to provide an apparatus which is relatively simple in construction and which greatly facilitates placement of the graft.

Another object of the invention is to provide a method of the above character which is relatively simple and error free.

Additional objects and features of the invention will appear from the following description in which the preferred embodiments are set forth in detail in conjunction with the accompanying drawings.

BRIEF DESCRIPTION OF THE PREFERRED EMBODIMENTS

FIG. 2 is a cross-sectional view taken along the line 2—2 of FIG. 1.

FIG. 4 is an enlarged perspective view of a graft having a bifurcation incorporating the present invention.

FIG. 8 is a perspective view of the hook assembly forming a part of the minor deployment device shown in FIG. 6 to be utilized with the graft shown in FIG. 4.

FIGS. 9–19 are diagrams showing the method and apparatus utilized in deploying the graft of the present invention.

DESCRIPTION OF THE PREFERRED EMBODIMENTS

Figure 1:
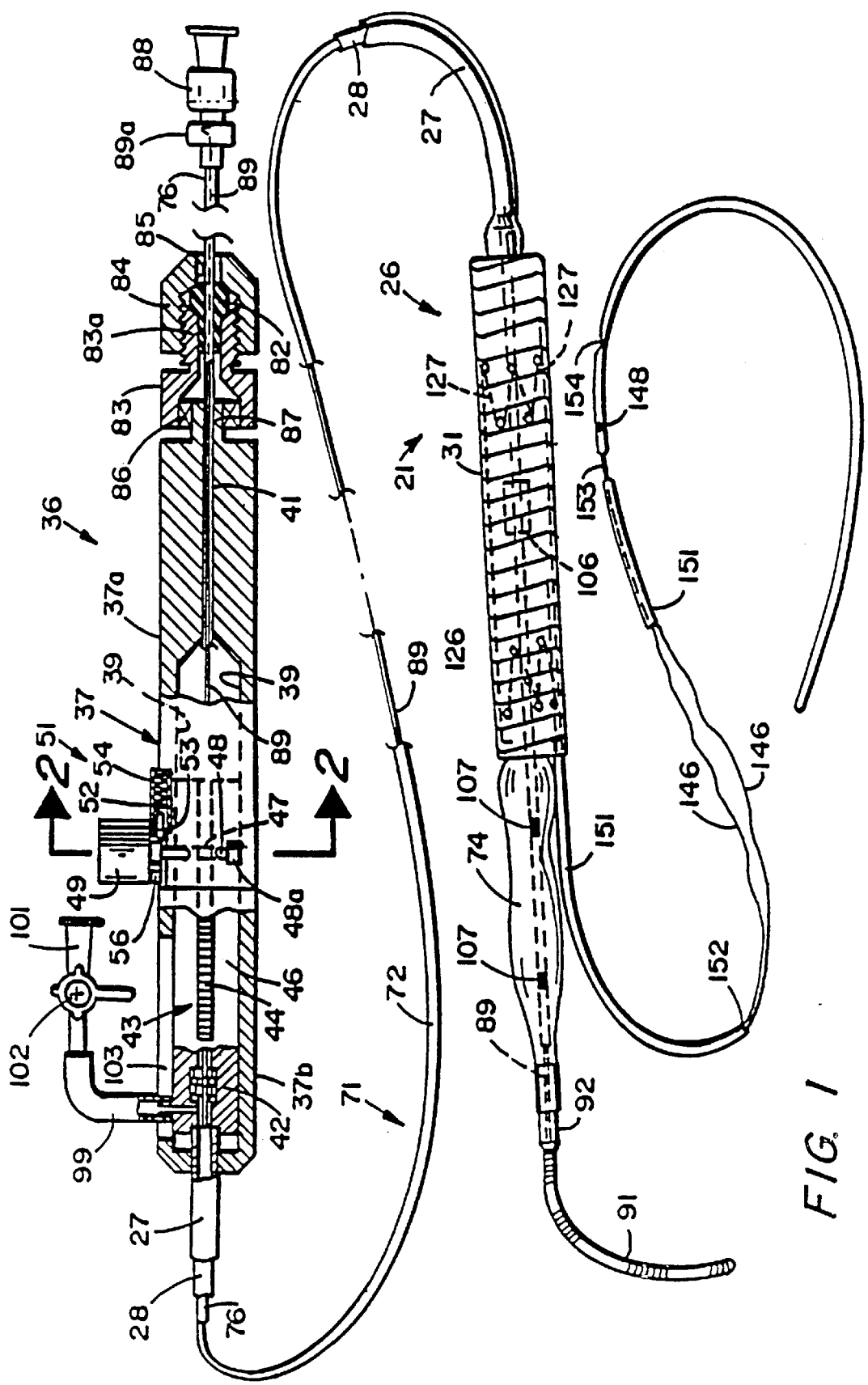
FIG. 1 is a plan view of the apparatus for deploying an endovascular graft having a bifurcation of the present invention in which the graft is disposed within the capsule ready for deployment.
Figure 17:
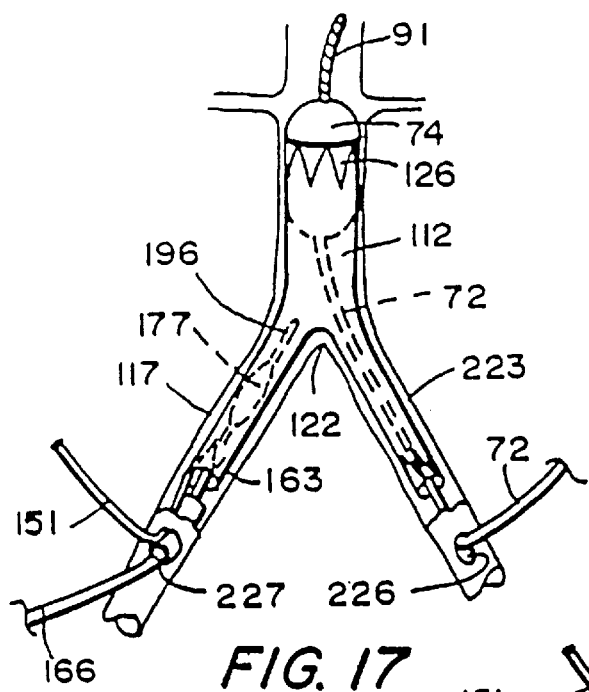
Figure 18:
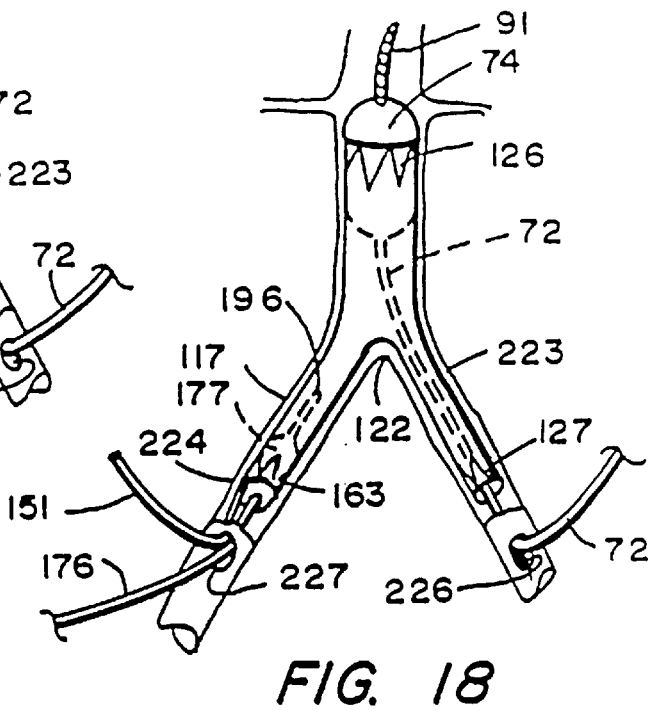
Figure 19:
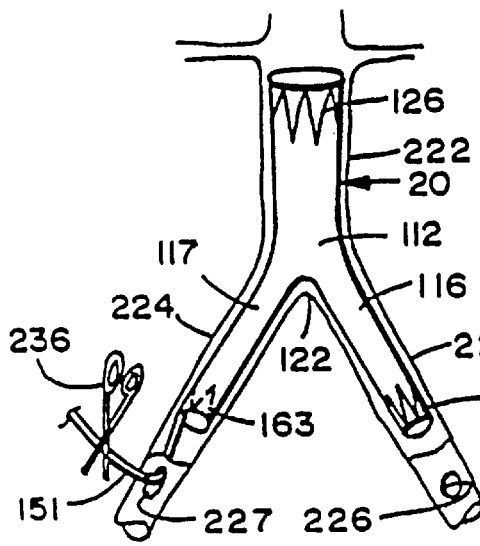

In general the graft having a bifurcation for repairing an aneurysm in the aorta extending to or beyond the aortic bifurcation in a patient comprising a main tubular body and first and second tubular legs joined to said main body in a bifurcation. The main body and the legs are formed of a flexible surgically implantable material. The main body and the first and second legs each have an opening therein in communication with the other openings. Expandable spring attachment means is secured to the main body adjacent the opening in the main body. Additional spring attachment means is secured to the first leg adjacent the opening in that leg. The major deployment device comprises a capsule catheter and a balloon catheter. The capsule catheter comprises a flexible elongate tubular member having proximal and distal extremities. A capsule is mounted on the distal extremity of the flexible elongate tubular member and has an open end. A graft is disposed within the capsule. The balloon catheter comprises a flexible elongate tubular member having proximal and distal extremities. A balloon is secured to the distal extremity of the flexible elongate tubular member of the balloon catheter. The flexible elongate tubular member of the balloon catheter extends through the graft and through the capsule in which the graft is disposed and through the flexible elongated tubular member of the capsule catheter. Retention means is carried by the flexible elongate tubular member of the balloon catheter and engages the graft. A control mechanism is provided and has a handle portion adapted to be grasped by a human hand and has first and second parts movable relative to each other. Means is provided for securing the flexible elongate tubular member of the capsule catheter to the first part. The flexible elongate tubular member of the balloon catheter extends through the first part and through the control mechanism. Means is carried by the control mechanism for causing movement of the first part with respect to the second part to thereby cause the capsule to be withdrawn from over the graft and permitting the retention means to retain the graft in position so that it is ejected from the capsule as the first part is moved relative to the second part.

The method for deploying a graft having bifurcation with a main body and first and second legs for deployment across the aortic bifurcation and into the first and second iliac arteries of a patient to repair an aneurysm therein comprising folding one of the legs of the graft so it lies substantially parallel to the main body of the graft, introducing the graft through the femoral artery until the distal portion of the graft is disposed proximal of the aortic aneurysm, securing the proximal extremity of the graft with the other leg of the graft being disposed in the first iliac artery, pulling down the folded over leg into the second iliac artery securing the distal extremity of the first leg of the graft in the first iliac artery and thereafter securing the second leg of the graft in the second iliac artery.

Figure 6:
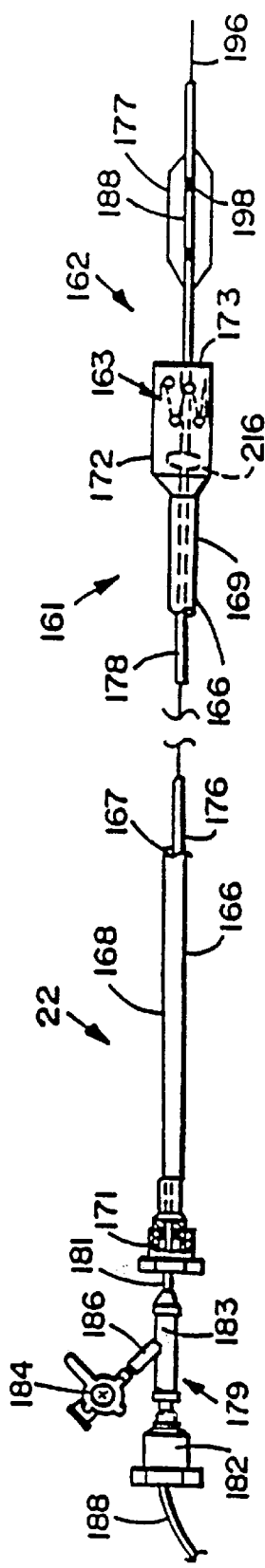
FIG. 6 is an elevational view partially in cross section of a minor deployment device utilized as a part of the apparatus for deploying the graft of the present invention.

The apparatus for deploying a graft 20 having a bifurcation of the present invention consists of a major deployment device 21 which is shown particularly in FIG. 1 and a minor deployment device 22 which is shown in FIG. 6. The major deployment device 21 incorporates a capsule catheter 26 which is very similar to a capsule catheter disclosed in co-pending application Ser. No. 07/553,530 filed Jul. 13, 1990. As disclosed therein, the capsule catheter 26 is provided with a flexible elongated tubular member 27 formed of a plastic which is loaded with a radiopaque material so that it will be visible under X-rays. An inner liner 28 of lubricous material is disposed within the tubular member 27. A flexible capsule 31 is secured to the distal extremity of the tubular member 27. The capsule can have a length ranging from 10 –40 centimeters and a diameter ranging from 6 –9 millimeters.

A control mechanism 36 is secured to the proximal extremity of the tubular member 27. The control mechanism 36 is provided with a multipart housing 37, a portion of which serves as a handle adapted to be engaged by the adult human hand. The housing 37 is formed in two parts 37a and 37b of a suitable material such as plastic. The part 37a serves as a cylindrical pinion housing which has a longitudinally extending bore 39 formed therein opening through one end thereof. A smaller bore 41 is provided in the pinion housing 37a and extends axially thereof and opens into the bore 39. The part 37b is secured to the part 37a by suitable means such as ultrasonic bonding. The part 37b serves as a rack housing. A generally cylindrical rack member 42 is slideably mounted in the bore 39. Means is provided for causing relative movement between the rack member 42 and the pinion housing 37a and consists of a rack and pinion assembly 43. The rack and pinion assembly 43 consists of a rack 44 which is mounted in a flat 46 provided on the rack member 42. The rack 44 is engaged by a pinion 47 mounted on a shaft 48. The shaft 48 extends through the pinion housing 37a and is provided with an enlargement 48a on one end. A knob 49 is mounted on the other end of the shaft 48 and is provided for rotating the shaft 48 by fingers of one hand of the operator. The other hand of the operator holds the control mechanism 36.

A detent assembly 51 is provided for permitting step-by-step rotation of the knob 49 in one direction but preventing rotation in an opposite direction. The detent assembly 51 consists of a plastic cylindrical housing 52 mounted in the wall of part 37a and has a plunger 53 slideably mounted therein which is yieldably urged in a direction towards the knob 49 by a coil spring 54. The plunger 53 serves as a detent which is adapted to engage the circumferentially spaced notches 56 provided in the knob 49. The notches 56 are shaped so that the knob 49 can only be rotated in one direction and not in the other direction.

The distal extremity of the rack housing 37b is provided with a bore 61 (see FIG. 3) which opens through the distal extremity of the same. A smaller bore 62 is provided within the rack member 42 and extends axially of the bore 61 and opens into the bore 61 and also opens through the proximal extremity of the rack member 42. A sliding seal housing 63 is provided within the bore 61 and is secured therein by suitable means such as an adhesive. The housing 63 is provided with a bore 64 which opens through the proximal extremity of the housing 63 and a smaller bore 66 extending axially of the bore 64 and opening into the bore 64 and opening through the distal extremity of the housing 63. The sliding seal housing 63 is provided with an annular recess 67 on its distal extremity which is adapted to receive the proximal extremity of the flexible elongate member 27 and is bonded thereto by suitable means such as an adhesive 28.

The major deployment device 21 also includes a balloon catheter assembly 71 of the type described in co-pending application Ser. No. 07/553,530 filed Jul. 13, 1990, and as disclosed therein consists of a flexible elongate tubular member in the form of a balloon catheter shaft 72 having a single lumen therein and formed of a suitable material such as irradiated polyethylene tubing. A separate balloon 74 is secured to the distal extremity of the balloon catheter shaft 72 and is formed of a suitable material such as polyethylene. The balloon catheter shaft 72 can have a suitable outside diameter such as 0.050" and extend into a metal hypo tube 76 formed of a suitable material such as stainless steel having a suitable outside diameter, for example 0.062". The metal tube 76 extends into the inner liner 28 and extends into the bore 66 of the sliding seal housing 63 and into the bore 64 where it engages a pair of the spaced-apart cylindrical members 77 and 78 formed of a suitable material such as polycarbonate and a pair of spaced-apart silicone O-rings 79 and 81, all of which are disposed within the bore 64 to form sliding seals. These sliding seals formed by the cylindrical members 77 and 78 in conjunction with the O-rings 79 and 81 serve to prevent body fluids from coming into contact with operating parts of the control mechanism 36 as for example, the rack and pinion assembly 43. The stainless steel hypo tube 76 extends rearwardly towards the proximal extremity through the passage 62 of the rack member 42 and into the bore 41 of the pinion housing 37a. A collet 82 is provided on the proximal extremity of the pinion housing 37a. Means is provided for permitting free rotational movement of the hypo tube 76 in a fixed longitudinal position and consists of a collet housing 83 having a threaded split cylindrical protrusion 83a with a collet cover 84 threaded thereon. The collet cover 84 has a hole 85 therein through which the hypo tube 76 passes. The collet housing 83 is rotatably mounted by an isolation ball bearing assembly 86 on a base 87 provided on the housing part 37a. When the collet cover 84 is rotated in one direction, the collet housing protrusion 83a is permitted to move to its normally open position to permit the collet 82 to open allowing the tube 76 to pass therethrough. When the collet cover 84 is rotated in an opposite direction it will close the housing protrusion 83a and lock the collet 82 onto the tube 76. A Luer-type fitting 88 is mounted on the proximal extremity of the hypo tube 76.

A stabilization wire 89 of a suitable material such as stainless steel and of a suitable diameter as, for example, 0.018" is disposed within the balloon catheter shaft 72 and extends the length thereof. The proximal extremity 89a of the pusher wire 89 is secured in a fixed position to the luer fitting 88 in a suitable manner such as by embedding in the wall of the fitting 88 as shown in FIG. 1. The pusher wire 89 extends through the lumen of the balloon catheter shaft 72 into the balloon 74 where it is fastened in a fixed position in the distal extremity of the balloon 74. A flexible, pre-shaped spring-like guide wire 91 is secured to the distal extremity of the balloon 74 by use of a plug 92 which also receives the distal extremity of the pusher wire 89.

Means is provided as a part of the control mechanism 36 for supplying liquids for injection into the capsule 31 and consists of a fitting 96 (see FIG. 3) which is mounted in the rack member 42 and which is provided with a bore 97 in communication with the bore 66. A flexible tube 99 is connected to the fitting 96 and is provided with a Luer-type fitting 101 having a stop cock 102 therein. The rack housing or cover 37b is provided with a slot 103 through which the tube 99 extends and can move longitudinally during rectilinear movement of the rack member 42.

A stabilization button 106 is mounted on the balloon catheter shaft 72 in a fixed position spaced a predetermined distance from the proximal extremity of the balloon 74 as for example, a distance of 5–10 centimeters. A pair of spaced-apart radiopaque markers 107 in the form of platinum bands are provided on the balloon catheter shaft 72 within the balloon 74. The endovascular graft 20 having a bifurcation is shown in FIG. 4. The graft 20 has many characteristics which are similar to the expandable intraluminal vascular graft disclosed in co-pending application Ser. No. 07/553,530 filed Jul. 13, 1990. However, the graft 20 differs significantly from the graft disclosed therein in that it is provided with a bifurcation as hereinafter described. The graft 20 is an expandable intraluminal vascular graft which is provided with a main deformable cylindrical body 112 having an open end 113. The body 112 is provided with a bifurcation or crotch 114 at the other end which opens into first and second legs 116 and 117, having open ends 118 and 119 generally opposite the open end 113. Continuous walls form the body 112 and the legs 116 and 117 and are woven of surgically implantable material such as Dacron-type fiber. One material found to be particularly satisfactory is a USCI DeBakey soft woven Dacron vascular prosthesis. The main body 112 can have a length ranging from 5 to 30 centimeters with each of the legs having a length ranging from 2 to 15 centimeters. The body 112 can have a maximum expandable diameter ranging from 12 to 30 millimeters whereas the legs 116 and 117 can have maximum diameters ranging from 6 to 12 millimeters.

Radiopaque markers 121 are provided on the main body 112 and also on the legs 116 and 117 and can be formed of a suitable material such as lengths of platinum wire secured to the fabric of the graft by suitable means such as Dacron sutures.

Expandable spring attachment means 126 is secured to the expandable main body adjacent the opening 113. Also expandable spring attachment means 127 is secured to the first leg 116 adjacent the opening 118. These expandable spring attachment means 126 and 127 serve as anchoring means for securing the graft 20 to vessel wall in which the graft 20 is disposed. The expandable spring attachment means 126 is constructed in a manner similar to that described in co-pending application Ser. No. 07/553,350 filed Jul. 13, 1990, and serves to yieldably urge the opening 113 in the main body 112 from an initial compressed or collapsed position to a subsequent expanded position. Similarly, the expandable spring attachment means 127 serves to yieldably urge the open end 118 from an initial compressed or collapsed position to a subsequent expanded position. As explained in said co-pending application Ser. No. 07/553,350 filed Jul. 13, 1990, the expandable spring attachment means 126 and 127 are formed of a plurality of vees 131 with the apices 132 being formed with helical coil springs 133 to yieldably urge the legs 134 and 136 of each of the vees 131 outwardly in directions in the planes in which the vees lie. As disclosed in the co-pending application Ser. No. 07/553,350 filed Jul. 13, 1990, the apices 132 lie in three longitudinally spaced-apart parallel planes extending transversely of the axis of the expandable spring attachment means in which the first plane is disposed internally of the open end and the second plane lies in a position which is external of but in close proximity to the open end and the third plane is spaced a substantial distance beyond the open end.

Hook-like elements 141 are provided at the apices 132 which are disposed beyond the open end 113 for the attachment means 126 and the open end 118 for the attachment means 127. The hook-like elements 141 are bonded to the legs 136 of the vees 131 by suitable means such as welding. The hook-like elements 141 have hooks 142 which are of a length which is sufficient to penetrate into the vessel wall and slightly beyond the vessel wall in which the graft is to be placed. The expandable spring attachment means 126 and 127 are secured to the graft by Dacron polyester suture material 144 as shown particularly in FIG. 4.

A pull line 146 is secured to the leg 117 in a region which is closely approximate the end of the leg 117 at the opening 119. The pull line can be formed of a suitable material such as Nylon having a diameter from 0.005"–0.010". The pull line 146 is continuous and extends through small holes 147 provided in the material forming the graft 20. The pull line 146 which is doubled over onto itself and has a doubled-over length of approximately 40–60 centimeters with the ends of the pull line 146 being tied together in a knot 148. A lead tube 151 with a lumen 152 is positioned over the pull line 146 so it is adjacent the leg 117. The lead tube 151 is necked down at 153 by suitable means such as by heat in a region distal of the knot 148 (see FIG. 4) so that the lead tube 151 is retained on the pull line 146. A cutout 154 is provided in the lead tube 151 proximal of the knot 148.

Figure 5:
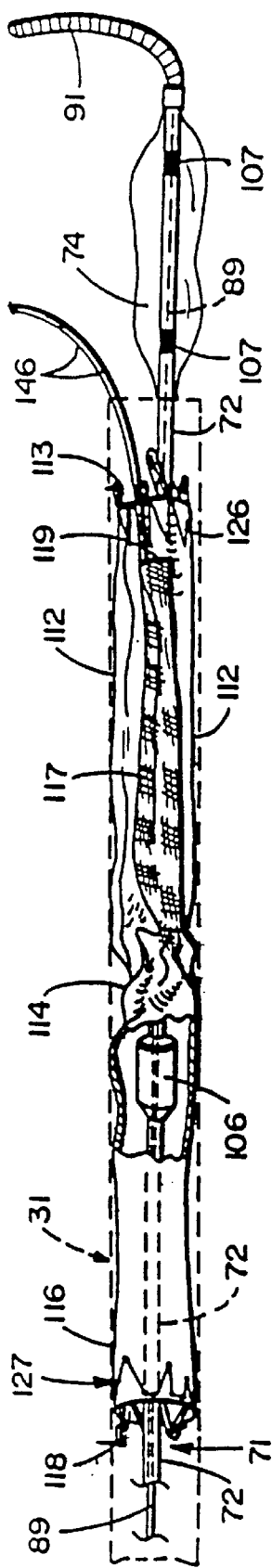
FIG. 5 is an enlarged schematic view of the capsule showing the manner in which the graft having bifurcation is stored therein for deployment.

The balloon catheter assembly 71 is disposed within the capsule 31 in a manner also shown in FIG. 5 in which the balloon tube or shaft 72 extends coaxially of the main body of the graft 112 coaxially of the first leg 116. The stabilization button 106 is preferably disposed within the graft in a position which is just proximal of the bifurcation or crotch 114. By positioning the pusher button 106 where shown in FIG. 5, it is near to the major portion of the material forming the graft 20 which is folded up within the capsule 31. This is desirable because the mass of material provided in that region of the capsule facilitates pushing the graft 20 out of the capsule as hereinafter described.

The minor deployment device 22 as particularly shown in FIG. 6 consists of a capsule catheter 161, a balloon catheter 162 and a separate expandable spring attachment means 163. Th separate balloon catheter 162 is shown in greater detail in FIG. 7 and the separate spring attachment means 163 is shown in FIG. 8. The capsule catheter 161 consists of a flexible tubular member 166 formed of a suitable material such as polyethylene having an inside diameter ranging from 0.050 to 0.080"and an outside diameter ranging from 0.075 to 0.100". The tubular member 166 can have a suitable length as for example, 15–25 centimeters. The tubular member 166 has a lumen 167 extending the length thereof and has proximal and distal extremities 168 and 169. A conventional Tuohy Borst adapter 171 is mounted on the proximal extremity 168. A small capsule 172 formed of suitable material such as stainless steel is mounted on the distal extremity 169 of the tubular member 166. It can be of a suitable size, as for example a length of 10 to 30 millimeters and an inside diameter of 4 to 6 millimeters with a wall thickness ranging from 0.006 to 0.015". The capsule 172 is provided with an open end 173 through which the separate expandable spring attachment means 163 is adapted to be inserted.

Figure 7:
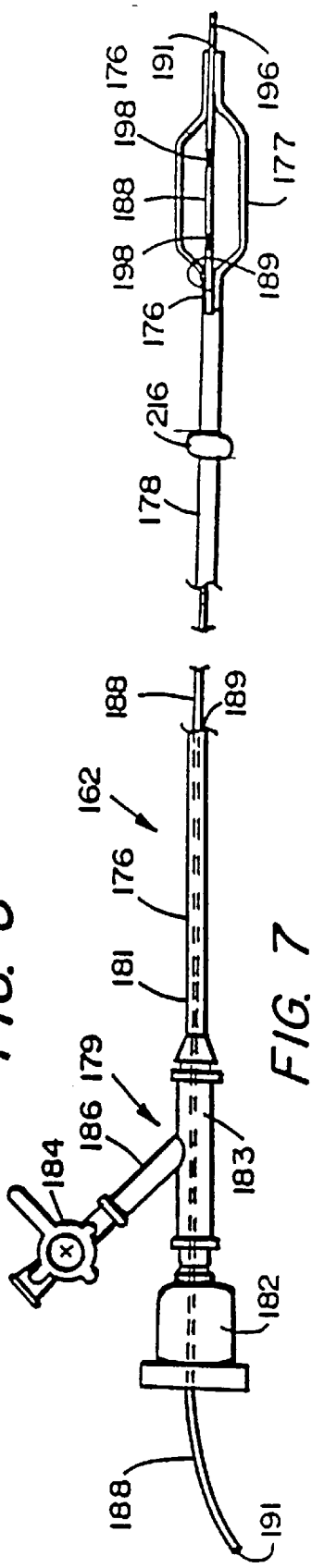
FIG. 7 is an elevational view partially in cross section of the balloon dilatation catheter utilized in the minor deployment device shown in FIG. 6.

The balloon catheter 162 as shown in FIG. 7 consists of a flexible elongated tubular member 176 formed of a suitable material such as polyethylene and which serves as the balloon shaft and is provided with an outside diameter ranging from 0.040 to 0.0060 and an inside diameter ranging from 0.015 to 0.030". An expandable balloon 177 is formed integral with the flexible elongate tubular member 176 near the distal extremity thereof. The balloon 177 is formed of the same polyethylene material as the tubular member 176 and can have a diameter ranging from 6 to 12 millimeters and a length ranging from 1 to 2 centimeters. A wye adapter 179 is mounted on the proximal extremity 181 of the flexible elongated tubular member 176. A Tuohy Borst adapter 182 is mounted on the main arm 183 of the wye adapter 179. A stop cock 184 is mounted on the side arm 186 of the wye adapter 179.

An additional elongate flexible tubular member 188 of a suitable material such as polyethylene is provided and extends from the Tuohy Borst adapter 182 through the lumen 189 provided in the tubular member 176 and through the balloon 177 where the distal extremity of the elongate flexible tubular of the member 188 is bonded to the distal extremity of the tubular member 176 to provide an airtight seal for the balloon 177. The tubular member 188 is provided with a lumen 191 extending the length thereof as adapted to receive a guide wire 196 of a suitable size as for example, one having a diameter of 0.018"so that the guide wire 196 can extend through the tubular member 176 and through the balloon 177 and extend beyond the distal extremity of the tubular member 176. The guide wire 196 is of a conventional type and is utilized for guiding the balloon catheter as hereinafter described. A pair of spaced-apart radiopaque markers of a. suitable material such as gold bands 198 are provided on the tubular member 188 within the balloon 177.

The coaxial annular space between the exterior of the tubular member 188 and the interior of the tubular member 176 serves as an annular balloon inflation passage and is in communication with the side arm 186 so that the inflation and deflation of the balloon can be controlled by the stop cock 184.

The expandable spring attachment means 163 shown in FIG. 8 has a construction very similar to the expandable spring attachment means 126 and 127 hereinbefore described. The expandable spring attachment means 163 is provided with a plurality of vees 201 having apices 202 formed by coil springs 203 which have legs 204 and 206 expandable and contractible within the plane of the vee. The vees 201 are configured in such a manner so that the apices 202 lie in only two spaced-apart parallel planes perpendicular to the longitudinal axis of the expandable spring attachment means, rather than the three planes disclosed for expandable spring attachment means 126 and 127. Hook-like elements 207 are bonded to the legs or struts 204 or 206. The hook-like elements 207 are provided with hooks 208 which face outwardly of the expandable spring attachment means and in a direction towards the other end of the spring attachment means. Additional hook-like elements 209 are provided on the other end of the spring attachment means 163 by bonding the same by suitable means such as welding to the struts 204 and are provided with hooks 211 which face outwardly and extend in an opposite direction to the hooks 208, toward the other end of the spring attachment means. In this way it can be seen that the hooks 208 and 211 face in opposite directions, hooks 208 being angled slightly distally and hooks 211 being angled slightly proximally, and serve to prevent distal and proximal migration of the graft leg 117 to which the expandable attachment means 163 is attached as hereinafter described.

The expandable spring attachment means 163 is adapted to be compressed and mounted within the capsule 172 as shown particularly in FIG. 6. Means is provided for pushing the expandable spring attachment means 163 out of the open end 173 of the capsule 172 and consists of a stabilization button 216 which is formed on the balloon shaft or flexible elongate tubular member 176. The pusher member 216 can be formed in a suitable manner such as by forming a ring of longitudinally compressed polyethylene on the shaft 176. operation and use of the apparatus hereinbefore described for performing the method of the present invention for deploying an endovascular graft having bifurcation may now be briefly described as follows.

In conjunction with the diagrams which are set forth in FIGS. 9–19, let it be assumed that it is desired to repair an aneurysm in the abdominal aorta 222 close to or involving the aortic bifurcation 221 and possibly involving the left and right iliac arteries 223 and 224 in a human patient. In this example, the left iliac artery 223 is referred to as the first iliac artery, and the right iliac artery 224 is referred to as the second iliac artery. Graft legs 116 and 117 are identified similarly. Initially the patient is prepared with either general, regional, or local anesthesia. A cut-down is performed in the left femoral artery as indicated by the opening 226 in the first leg 223. Similarly, a cut-down or percutaneous access is performed in the right femoral artery as indicated by the opening 227 in the second leg 224. A guide wire 231 of a conventional type, as for example a guide wire having a diameter of 0.038", is introduced through the opening 226 in the left femoral artery 223 and then is passed over the aortic bifurcation 221 and down through the right artery 224 and out through the opening 227 in the right femoral artery. This procedure is accomplished in a conventional manner under fluoroscopy as shown in FIG. 9.

Thereafter as shown in FIG. 10 the lead tube 151 which. is extending out of the distal extremity of the capsule 31 is threaded over the guide wire 231 extending out of the hole 226 in the first artery 223 and thence into the left cut-down or hole 226 and over the guide wire 231 in the left artery, over the guide wire 231 in the aortic bifurcation 221 and then down the second artery 224 through the right cut-down 227 so that the distal extremity of the lead tube 151 extends for a substantial distance out of the cut-down 227. During the time that the lead tube 151 is being advanced, the distal extremity of the guide wire 231 is caused to pass through the cut-out 154 so that the distal extremity of the guide wire 231 is accessible and can be held steady while the lead tube 151 is advanced over it.

Thereafter, the guide wire 231 can be pulled out by grasping the proximal extremity of the guide wire 231 adjacent the cut-out 154 in the lead tube 151 pulling out the guide wire 231 while holding the distal extremity of the lead tube 151 so as to prevent the lead tube 151 from being pulled back into the cut-down 227. The distal extremity of the lead tube 151 is then clamped with a hemostat 236 as shown in FIG. 11 to be sure that the lead tube 151 is not pulled back into the cut-down 227 during future steps in the method of the present invention. The major deployment device 21 is then introduced into the left cut-down 226 by first passing the balloon guide wire 91 and then the balloon 74 through the left cut-down 226 followed by the capsule 31, which is advanced to the position shown in FIG. 11 by pushing on the tubular member 27. During the advancement, the operator may need to place gentle traction on the lead tube 151 to facilitate advancement of the capsule 31 toward the aortic bifurcation 221. When the capsule 31 reaches the aortic bifurcation 221, it is necessary for the operator holding the lead tube 151 to permit more of the lead tube 151 to enter the cut-down 227 to permit further advancement of the capsule 31 up the aorta so that the proximal spring attachment means 126 of the graft 20 within the capsule 31 can be positioned in a region which is 1–2 centimeters proximal of the proximal extremity of the aneurysm to be corrected by the graft 20 being deployed. As shown in FIG. 12 the distal extremity of the capsule 31 is deployed well beyond the aortic bifurcation 221. As soon as the physician has determined that the capsule 31 is in the proper position, the physician uses one hand to hold the control mechanism 36 while at the same time using the fingers of the other hand to rotate the knob 49 and the pinion 47 to retract the rack member 42. This causes retraction of the tubular member 27 and the capsule 31 mounted thereon while the hypo tube 76 is retained in a stationary position by the collet 82 that is retained by the collet housing 83. As the capsule 31 is withdrawn, the stabilization button 106 carried by the tubular member 72 in engagement with the graft 20 as shown particularly in FIG. 5 causes the graft 20 to be gradually ejected from the capsule 31 as the capsule 31 is withdrawn. Upon continued retraction of the capsule 31, the proximal expandable spring attachment means 126 will clear the capsule 31 and will spring outwardly to cause the hooks 142 carried thereby to come into engagement with the aortic vessel wall proximal to the aneurysm to be repaired as shown in FIG. 12.

Figures 13, 14:
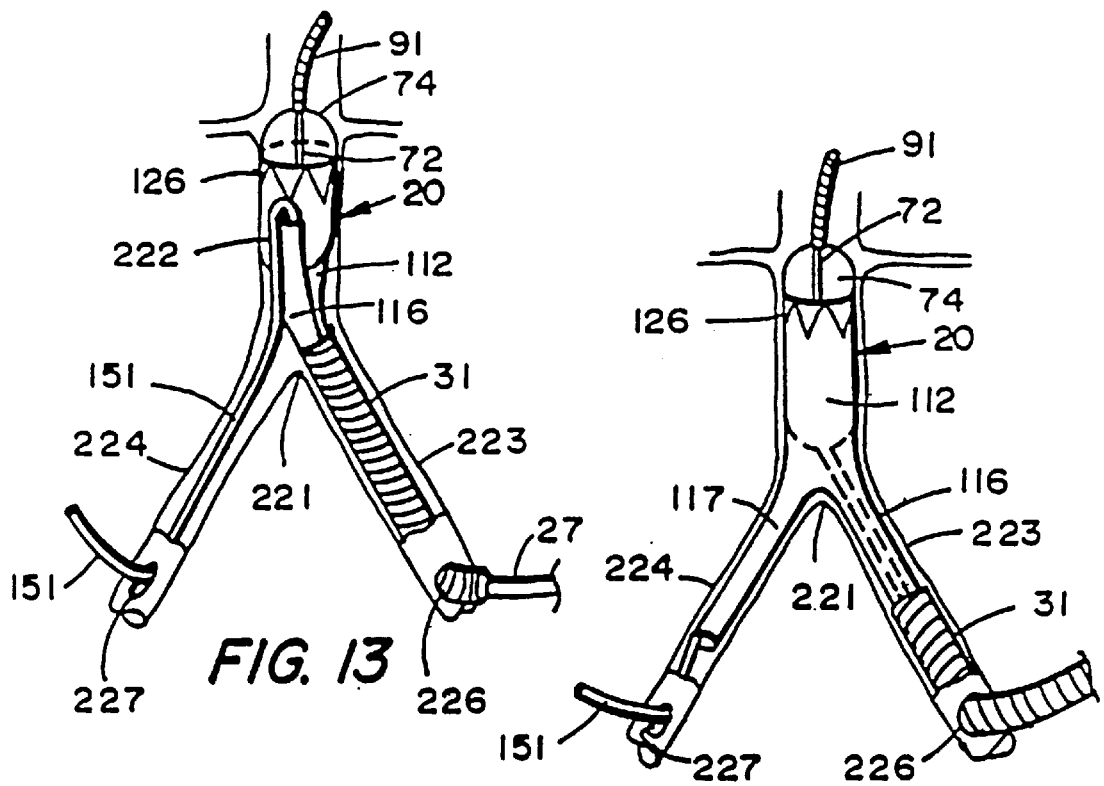

The physician, using one hand to hold the control mechanism 36, uses his other hand to release the collet 82 in order to unlock the tube 76 by rotating the collet cover 84 relative to the control mechanism 36. The physician repositions the hand not holding the control mechanism 36 so as to grasp the portion of the metal hypo tube 76 extending proximally of the control mechanism 36. The hypo tube 76 is then pulled rearwardly or proximally. The balloon 74 is thereby drawn into the proximal extremity of the main body portion 112 of the graft 20 as shown in FIG. 13 so that the intermediate portion of the balloon 74 is in general registration with the expandable spring attachment means 126. The balloon 74 is then inflated by supplying gas to the balloon inflation lumen by attachment of a syringe or other suitable inflation means to the Luer fitting 88. Upon inflation of the balloon 74 the hooks 142 carried by the proximal expandable spring attachment means 126 are firmly seated circumferenctially in the normal aortic wall proximal to the aortic aneurysm. With the balloon 74 still inflated and firmly holding the proximal attachment means 126 against the aortic wall, the capsule 31 is then further retracted by holding tube 76 in fixed position relative to the patient with one hand and retracting the handle 36 with the other hand in order to expose the entire length of the second leg 117 as shown in FIG. 13. The capsule 31 is still further retracted to clear most of the first leg 116 as shown in FIG. 14. As this is being accomplished, the second leg 117 of the graft 20 is pulled down into the artery 224 by pulling on the lead tube 151 so that the entire length of the leg 117 of the graft 20 is disposed in the arterial vessel 224 and extends substantially below the bifurcation 221 and below the aneurysm which is to be repaired. Further retraction of the capsule 31 is accomplished by holding tube 76 fixed with one hand and retracting the handle 36 with the other hand until the distal expandable spring attachment means 127 carried by the first leg 116 clears the capsule 31 and springs into engagement with the wall of the arterial vessel 223. It should be appreciated that during the foregoing procedures, the balloon 74 remains inflated in the attachment means 126 to prevent any accidental dislodgement of the Attachment means 126 during the removal of the capsule 31 and during the placement of the second leg 117 of the graft 20 into the artery 224 by pulling on the lead line 151.

Figures 15, 16:
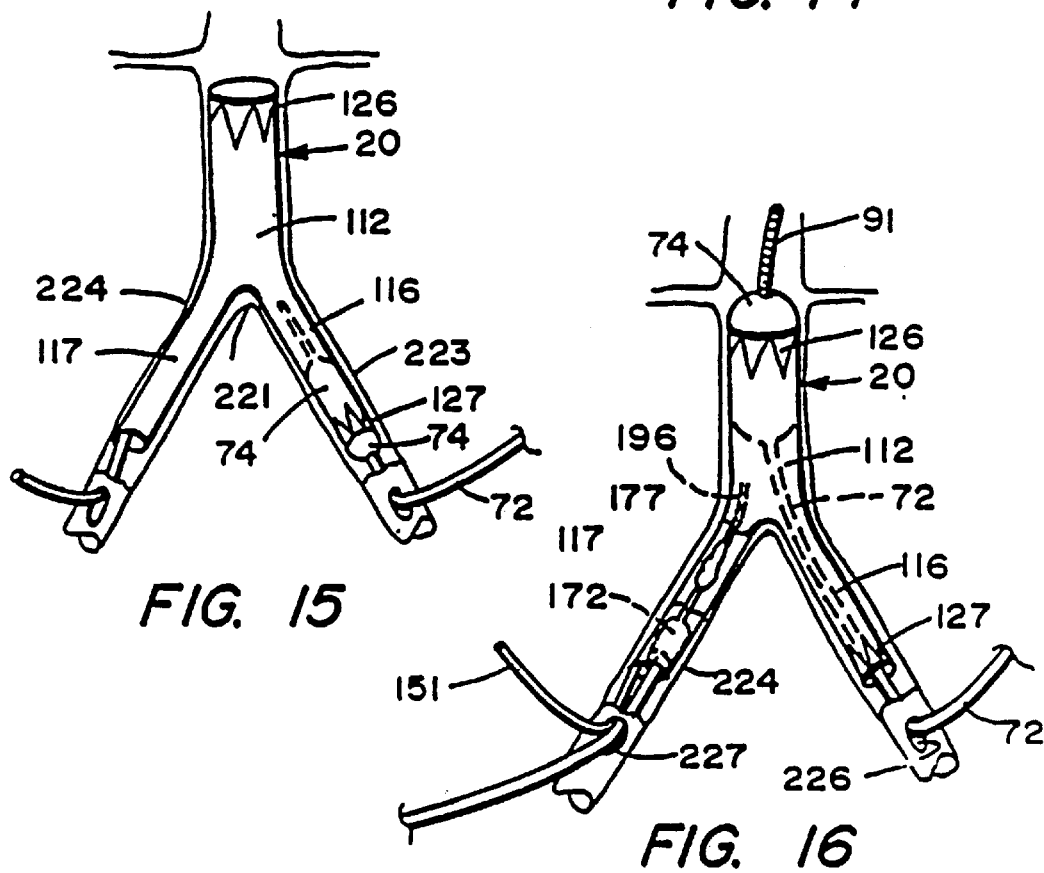

The balloon 74 is then deflated so that it is in a collapsed position.and the balloon is withdrawn from the attachment means 126 into the first leg 117 until its intermediate portion is in registration with the attachment means 127. The balloon 74 is then reinflated to expand the hooks 142 of the attachment means 127 into firm engagement with the arterial wall of the vessel 223 as shown in FIG. 15.

After this has been accomplished, the balloon 74 is again deflated and is advanced up through the main body of the graft 112 and again into the attachment means 126. The balloon 74 is then reinflated as shown in FIG. 16 and serves to hold the graft 20 in place while the procedures for securing the distal extremity of the second leg 117 are accomplished. It is likely in many instances that this step of again securing the proximal extremity of the graft by inflating the balloon in the attachment means 126 may be unnecessary. However to ensure that the graft 20 will not move after it has been deployed, as additional insurance, the balloon 74 can be positioned in the attachment means 126 and reinflated.

The minor deployment device 22 is next utilized. The guide wire 196 forming a part thereof is introduced through the cutdown 227 into the second artery 224 so that it extends into the second leg 117 of the graft 20 and beyond the bifurcation. The balloon catheter 162 is threaded onto or advanced over the guide wire 196. The balloon catheter 162 is disposed within the capsule catheter 161. The minor deployment device 22, with its balloon catheter 162 and capsule catheter 161, is advanced into the cutdown 227 while applying gentle traction to the lead tube 151 to keep the second leg 117 of the graft 20 taut. The balloon 177 and the capsule 172 are thus introduced into the second leg 117. The capsule 172 is positioned so that when the expandable spring attachment means 163 contained therein is deployed therefrom, the spring attachment means 163 will be at the distal extremity of the second leg 117 of the graft 20 as shown in FIG. 16. The expandable spring attachment means 163 is then forced out of the capsule 172 by the physician using one hand to grasp the wye adapter 179 and hold it in a fixed position relative to the patient and using the other hand to grasp the Tuohy Borst adapter 171 and gradually withdraw the same to retract the capsule 172 from over the expandable spring attachment means 163 which is held in the desired position by the stabilization button 216 carried by the tubular member 176. As soon as the expandable spring attachment means 163 clears the capsule 172 it will spring out with one row of hooks 208 moving into engagement with the distal extremity of the second leg 117 and with the other row of hooks 211 moving into engagement with the wall of the arterial vessel 224. Alternatively the capsule 172 is positioned so that when the expandable spring attachment means 163 contained therein is displaced therefrom, the expandable spring attachment means 163 is disposed within the second leg 117 so that both rows of hooks 208 and 211 move into engagement with the distal extremity of the leg 117 and engage the wall of the vessel 224.

In order to firmly implant the hooks 208 and 211 of the expandable spring attachment means 163, the balloon 177 in its deflated condition is brought down into the attachment means 163 so that its intermediate portion is disposed within the attachment means 163. This is accomplished by pulling on the wye adapter 179 which applies a pulling force to the tubular member 176 to pull the balloon 177 towards the distal extremity of the leg 117 of the graft 20 while at the same time withdrawing, if so desired, the capsule catheter 161 by pulling on the adapter 171 which applies a pulling force to the tubular member 166. As soon as the balloon 177 is in the proper position, the balloon 177 is inflated by suitable inflation means as, for example, a syringe attached to the stop cock fitting 184 and inflating the balloon 177 to the desired pressure to force the hooks 208 and 211 firmly into the distal extremity of the leg 117 of the graft 20 and the arterial vessel 224.

After the inflation of the balloon 177 has been accomplished, the balloon 177 can be deflated by removing the syringe and opening the stop cock 184. The balloon catheter 162 and the capsule catheter 161 then can be removed through the cutdown 227 so that all that remains is the lead tube 151 extending through the cutdown 227. The lead tube 151 is cut distal to the knot 148 in the vicinity of the necked down section 153 and the lead tube 151 is pulled off of the pull line 146. One end of the Nylon pull line 146 is then grasped to pull out the Nylon pull line 146 by having the free end travel up into the cutdown 227 and pass through the distal extremity of the leg 117 of the graft 20. It is then removed in its entirety through the cutdown 227. The right cutdown 227 is then repaired. Following that, the balloon 74 is deflated. The hypo tube 76 is retracted relative to the control mechanism 36 to move the balloon into engagement with the capsule 31. The collet 82 is then locked onto the hypo tube 76 by turning the knob 84 relative to the control mechanism 36. The control mechanism 36 is then withdrawn to remove the capsule catheter 27, the balloon catheter shaft 72, and the balloon 74 through the cutdown 226. The left cutdown 226 is then repaired. This completes the steps for deployment of the graft 20 across an aortic bifurcation to repair an aneurysm. The patient can then be brought out of general anesthesia if employed.

It should be appreciated that the graft having bifurcation can have legs of various lengths depending upon the type of aneurysm which is to be repaired. For example, one leg can be longer than the other. The legs can both be short in cases in which the aneurysm has a short distal aortic neck and does not include the iliac arteries. They would be longer in aneurysms which involve the iliac arteries as well. It is generally desirable that the graft extend at least one centimeter beyond the most distal portion of the most distal aneurysm in the vessels.

From the foregoing it can be seen that there has been provided a graft having a bifurcation in which the main body of the graft as well as the legs are firmly attached in the arterial vessels so that they accidentally cannot become dislodged from the location in which they are fixed in the arterial walls. The method which is utilized for deploying the graft with legs is relatively simple and can be accomplished within a relatively short period of time. The major and minor deployment devices which are utilized in the procedure are constructed in such a manner that they are easy to utilize with a minimum of training. The use of a folded-over second leg of the graft in the capsule makes it unnecessary to move the main body of the graft as high in the aorta as would be otherwise necessary in order to permit the second leg of the graft to clear the aortic bifurcation thereby permit the second one to be placed in the second iliac artery. Thus, the risk incurred by moving the graft and its capsule and any associated debris past the renal arteries located well above the aortic bifurcation is greatly reduced thereby reducing the chance of occluding the renal arteries and causing embolization to the renal arteries.

What is claimed is:

1. A method for intraluminal emplacement of a graft in a bifurcated vessel of a patient, the method comprising:
   providing a graft having a main body, with a first self-expanding device, the graft further having a first leg portion and a second leg portion with a second self-expanding device;
   inserting the graft intraluminally into a main vessel of a patient, the main vessel having a bifurcation forming a first minor vessel and a second minor vessel;
   positioning the main body of the graft in the main vessel;
   releasing the first self-expanding device and the main body of the graft in the main vessel;
   positioning the second leg portion of the graft in the second minor vessel; and
   releasing the second self-expanding device and the second leg portion of the graft in a second minor vessel.

2. The method of claim 1, further comprising the steps of:
   providing at least one radiopaque marker disposed on the graft;
   using fluoroscopy to examine the radiopaque marker to determine whether the graft is misaligned; and
   aligning the graft to provide an unobstructed flow of fluid through the graft.

3. A method for emplacement of a bifurcated graft for repairing an aotic aneurysm proximate an aortic bifurcation joining first and second iliac arteries of a patient, the method comprising:
   providing a graft having a main body, a first leg portion, a second leg portion, and a self-expanding affixation system operatively associated with the main body and at least one leg portion;
   passing the graft through a first iliac artery of a patient;
   positioning the graft proximate the aortic aneurysm having a superior end; and
   permitting the affixation system to self-expand to thereby attach the main body of the graft proximate the superior end of the aortic aneurysm and the first leg portion in the first iliac artery.

4. The method of claim 3, further comprising the step of using fluoroscopic means for visually inspecting a plurality of radiopaque markers located on the graft to determine if the graft is twisted or misaligned.

5. The method of claim 4, further comprising the step of aligning the graft to provide an unobstructed flow of fluid.

6. A method for intraluminal emplacement of a graft in a bifurcated vessel of a patient, the method comprising:
   providing a graft having a main body including a first self-expanding attachment system, the graft further having a first leg portion including a second self-expanding attachment system and a second leg portion;
   inserting the graft intraluminally into a main vessel of a patient, the main vessel having a bifurcation forming a first minor vessel and a second minor vessel;
   positioning the main body of the graft in the main vessel and the first leg portion in the first minor vessel;
   securing the first self-expanding attachment system and the main tubular body of the graft in the main vessel;
   securing the second self-expanding attachment system and the first leg portion of the self-expanding graft in the first minor vessel; and
   positioning the second leg portion of the graft in the second minor vessel.

7. The method of claim 6, further comprising the steps of:
   providing a first inflatable member configured to be positioned within the main vessel and the first minor vessel;
   positioning the first inflatable member within the main body;
   inflating the first inflatable member to secure the first self-expanding attachment system within the main vessel;
   deflating the first inflatable member;
   positioning the first inflatable member within the first leg portion; and
   inflating the first inflatable member to secure the second self-expanding attachment system within the first minor vessel.

* * * * *

UNITED STATES PATENT AND TRADEMARK OFFICE
CERTIFICATE OF CORRECTION

PATENT NO. : 6,214,038 B1
DATED : April 10, 2001
INVENTOR(S) : Alec A. Piplani, et al.

Figure 3:
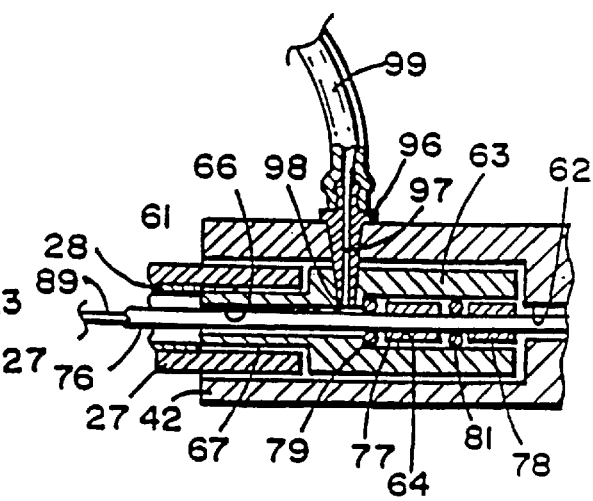
FIG. 3 is an enlarged cross-sectional view showing the sliding seal assembly utilized in the device shown in FIG. 1.

It is certified that error appears in the above-identified patent and that said Letters Patent is hereby corrected as shown below:

Drawing Sheet 3 of 6,
FIG. 3, change "28", to read -- 128 --.

Column 3,
Line 63, change "28", to read -- 128 --.

Column 6,
Line 59, change "0.0060", to read -- 0.060 --.

Signed and Sealed this

Sixth Day of November, 2001

Attest:

NICHOLAS P. GODICI
Attesting Officer   Acting Director of the United States Patent and Trademark Office